(12) United States Patent
Yum et al.

(10) Patent No.: US 12,109,329 B2
(45) Date of Patent: Oct. 8, 2024

(54) DIGITAL LIGHT FOUR-DIMENSIONAL PRINTING OF PROGRAMMABLE MORPHOLOGY AND MOTION STRUCTURES

(71) Applicant: Board of Regents, The University of Texas System, Austin, TX (US)

(72) Inventors: Kyung Suk Yum, Fort Worth, TX (US); Amirali Nojoomi, Arlington, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 909 days.

(21) Appl. No.: 17/055,798

(22) PCT Filed: May 23, 2019

(86) PCT No.: PCT/US2019/033704
§ 371 (c)(1),
(2) Date: Nov. 16, 2020

(87) PCT Pub. No.: WO2019/226874
PCT Pub. Date: Nov. 28, 2019

(65) Prior Publication Data
US 2021/0228776 A1    Jul. 29, 2021

Related U.S. Application Data

(60) Provisional application No. 62/675,469, filed on May 23, 2018.

(51) Int. Cl.
*A61L 27/52* (2006.01)
*B33Y 10/00* (2015.01)
(Continued)

(52) U.S. Cl.
CPC ............... *A61L 27/52* (2013.01); *B33Y 10/00* (2014.12); *B33Y 30/00* (2014.12); *B33Y 40/20* (2020.01); *C08J 3/24* (2013.01); *B33Y 70/10* (2020.01)

(58) Field of Classification Search
None
See application file for complete search history.

(56) References Cited

U.S. PATENT DOCUMENTS

| 7,689,260 B2 | 3/2010 | Finch et al. |
| 7,968,650 B2 | 6/2011 | Tighe et al. |

(Continued)

FOREIGN PATENT DOCUMENTS

| CN | 101824124 A | 9/2010 |
| CN | 109762113 A | 5/2019 |

(Continued)

OTHER PUBLICATIONS

International Search Report for PCT/US2019/33704 mailed Sep. 27, 2019.
(Continued)

*Primary Examiner* — Anthony M Liang
(74) *Attorney, Agent, or Firm* — Thomas | Horstemeyer, LLP

(57) ABSTRACT

The approach described herein uses the spatially and temporally controlled growth for programming 3D shapes and their motions, possibly with an unlimited number of degrees of freedom, could thus create dynamic 3D structures. The ability to program growth-induced 3D shapes and motions could transform the way engineering systems, such as robots, actuators, and artificial muscles, are designed. The concept is applicable to other programmable materials. The 2D printing approach for 3D material programming represents a scalable and customizable 3D manufacturing tech- (Continued)

nology, which can potentially be integrated with biological systems and existing 2D fabrication methods and devices for broader applications.

15 Claims, 13 Drawing Sheets

(51) Int. Cl.
    *B33Y 30/00*     (2015.01)
    *B33Y 40/20*     (2020.01)
    *C08J 3/24*     (2006.01)
    *B33Y 70/10*     (2020.01)

(56) References Cited

U.S. PATENT DOCUMENTS

| | | |
|---|---|---|
| 8,501,832 B2 | 8/2013 | Tighe et al. |
| 8,883,874 B2 | 11/2014 | Tighe et al. |
| 2007/0073130 A1 | 3/2007 | Finch et al. |
| 2008/0114123 A1 | 5/2008 | Tighe et al. |
| 2009/0280182 A1 | 11/2009 | Beck et al. |
| 2012/0212703 A1 | 8/2012 | Tighe et al. |
| 2013/0289135 A1 | 10/2013 | Beverley et al. |

FOREIGN PATENT DOCUMENTS

| | | |
|---|---|---|
| WO | 2005046470 A1 | 5/2005 |
| WO | 2009134414 A2 | 11/2009 |
| WO | 2009134414 A3 | 11/2009 |

OTHER PUBLICATIONS (Han, D et al.) "Micro 3D Printing of a Temperature-Responsive Hydrogel Using Projection Micro-Stereolithography"; Jan. 31, 2018; Scientific Reports 8, Article No. 1963.

(Nakayama, M et al.) "Poly(N-isopropylacrylamide)-based Smart Surfaces for Cell Sheet Tissue Engineering" Material Matters 2010, Downloaded Sep. 8, 2019 at https://www.sigmaaldrich.com/technical-documents/articles/material-matters/poly-n-isopropylacrylamide.html.

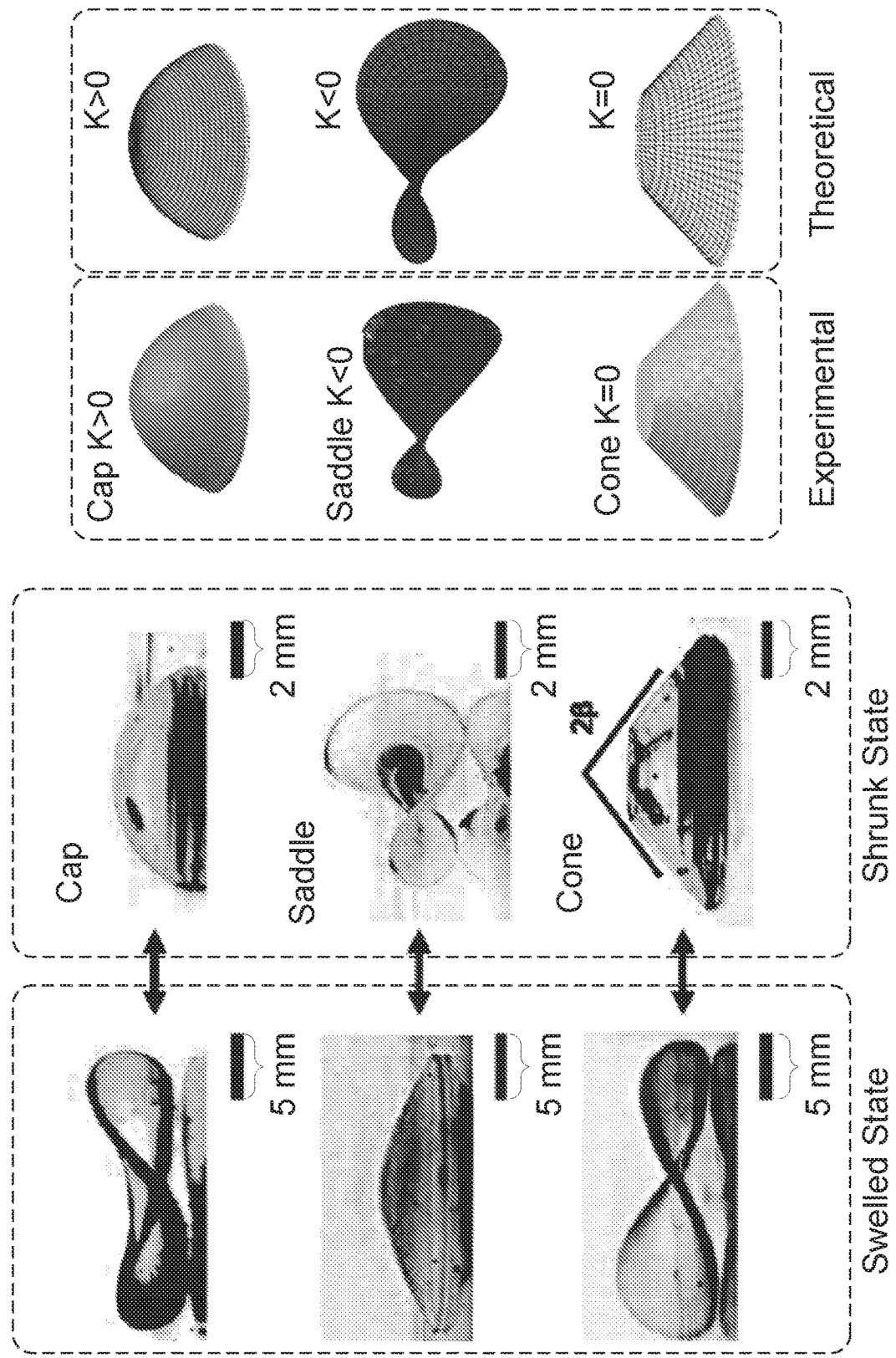

2 mm

Swelled State   5 mm          Shrunk State   2 mm

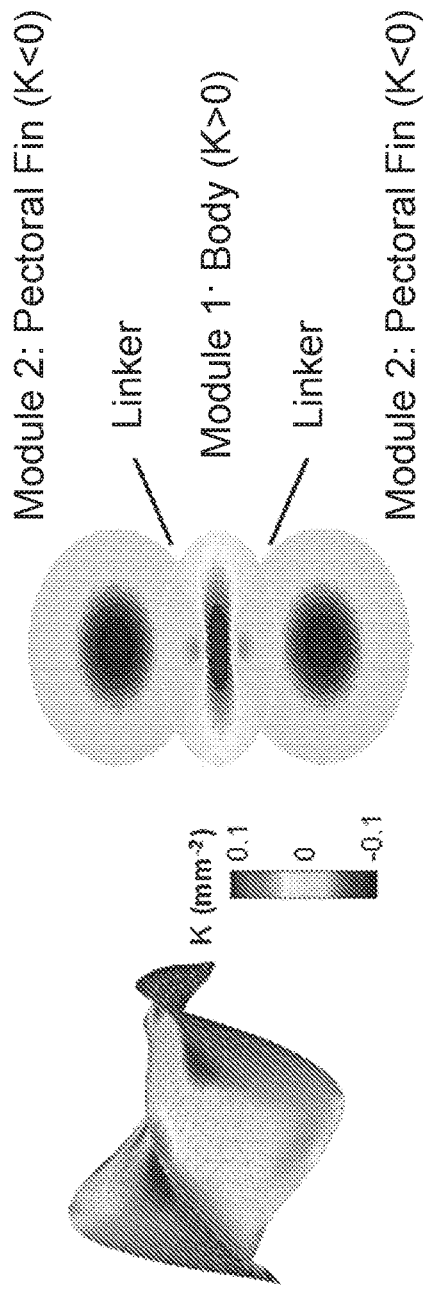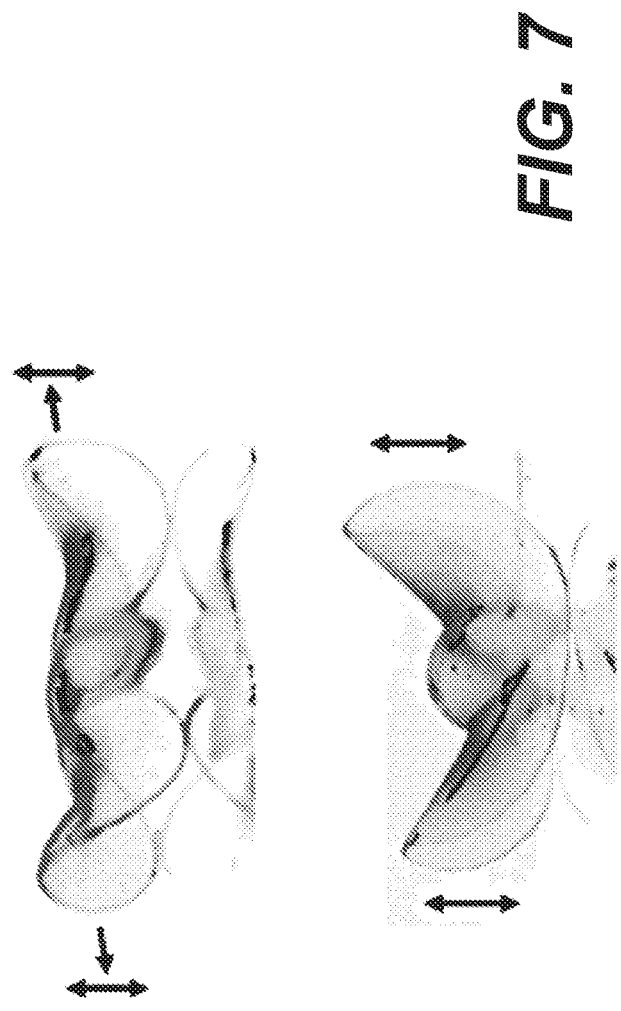
FIG. 7

DIGITAL LIGHT FOUR-DIMENSIONAL PRINTING OF PROGRAMMABLE MORPHOLOGY AND MOTION STRUCTURES

CROSS-REFERENCE TO RELATED APPLICATIONS

This application is a 35 U.S.C. § 371 National Stage Patent Application of Patent Cooperation Treaty Application number PCT/US2019/033704, filed on May 23, 2019, and titled "DIGITAL LIGHT FOUR-DIMENSIONAL PRINTING OF PROGRAMMABLE MORPHOLOGY AND MOTION STRUCTURES," which claims the benefit of priority to U.S. Provisional Application No. 62/675,469, filed May 23, 2018, the entire contents of both of which applications are hereby incorporated herein by reference.

BACKGROUND

Shape-morphing materials have applications in various fields, such as soft robotics, programmable matter, bioinspired engineering, and biomimetic manufacturing. Certain existing approaches use swellable hydrogel structures, shape-memory polymers, and liquid crystalline elastomers with fabrication methods, such as photo-patterning, self-folding, and three-dimensional (3D) printing. Although these approaches have been used to build self-shaping 3D structures with various geometries, reproducing complex 3D morphologies, for example, those shown in living organisms, let alone their complex movements, has not been achieved.

SUMMARY

A method of forming hydrogel structures programmed for motion between prescribed shapes is described. The method includes preparing a precursor solution, introducing the precursor solution into a cell, and exposing the precursor solution in the cell with light to form a hydrogel structure from the precursor solution. The hydrogel structure has continuously varying, spatially controlled compositions and thus material properties, such as degrees and rates of swelling and shrinking, achieved by spatial and temporal control of the light. The method can also include shape-morphing the hydrogel structure to form a prescribed 3D structure and its shape transformation between different shapes by heating or cooling the hydrogel structure.

In one example, the precursor solution includes a solution comprising a short-chain cross linker and a long-chain cross linker. As one example, the precursor solution includes a solution of N-isopropylacrylamide (NIPAm), N,N'-methylene bisacrylamide (BIS), and poly(ethylene glycol) diacrylate (PEGDA). With the precursor solution formed, exposing the precursor solution can include spatially and temporally controlling exposure of the precursor solution using dynamic light projection grayscale lithography. The dynamic light projection grayscale lithography can form a hydrogel with continuously varying, spatially controlled compositions and thus material properties, such as degrees and rates of swelling and shrinking, described by a growth function or a growth pattern. The density of the polymer network of the hydrogel increases with the light exposure time. The increase in the density in turn decreases the degrees and rates of swelling and shrinking of the hydrogel.

To form air-stable polymer structures, the method can also include washing the hydrogel structure, storing the hydrogel structure in water, increasing the temperature of the water to increase the repulsion of water by the hydrogel structure and transition the hydrogel structure to a polymer structure. The method can also include exchanging the water with an ionic solution, and removing the polymer structure from the ionic solution to permit the structure to dry and thereby form an air-stable polymer structure.

BRIEF DESCRIPTION OF THE DRAWINGS

For a more complete understanding of the embodiments and the advantages thereof, reference is now made to the following description, in conjunction with the accompanying figures briefly described as follows:

FIG. 3A illustrates shape-morphing 3D structures with axisymmetric target metrics according to various embodiments described herein.

FIG. 3B illustrates reconstructed images and theoretical shapes of the structures shown in FIG. 3A according to various embodiments described herein.

FIG. 7 illustrates a 3D structure developed based on a stingray model according to various embodiments described herein.

Figure 1:
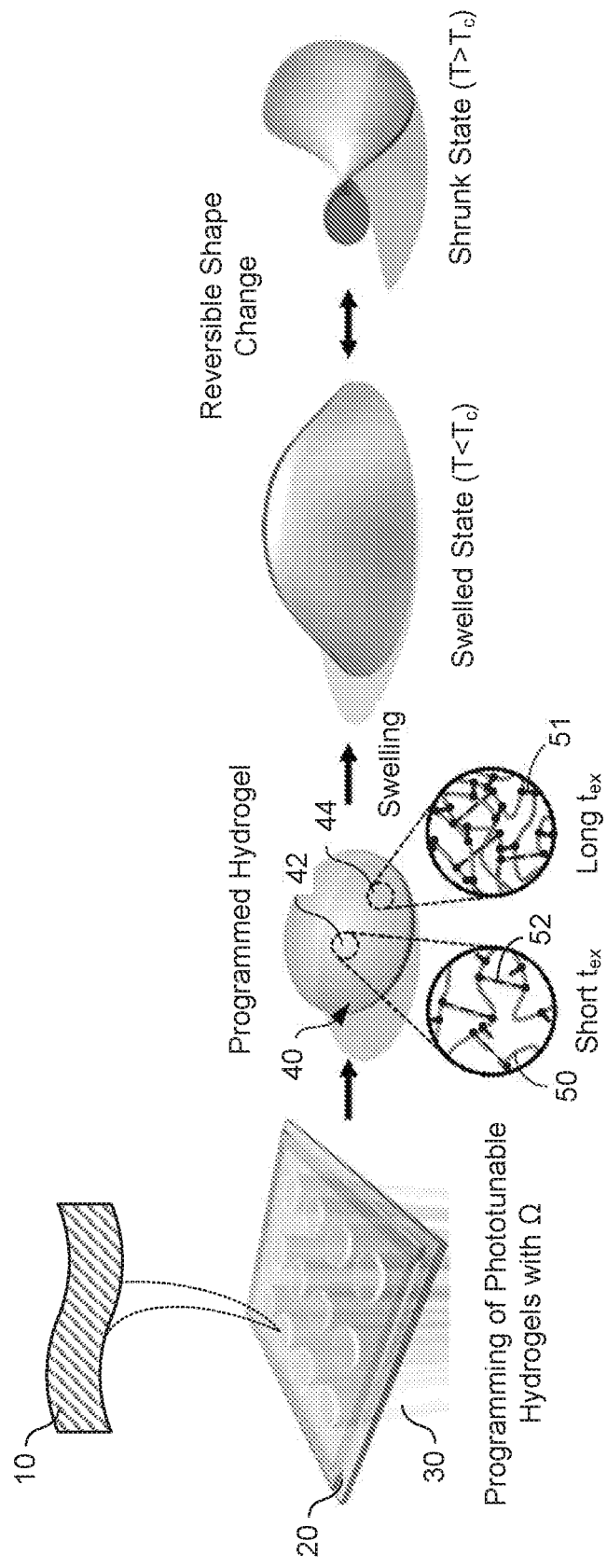
FIG. 1 illustrates an example of digital light 4D printing process, programming photo-tunable hydrogels to create 3D structures according to various embodiments described herein.

The drawings illustrate only example embodiments and are therefore not to be considered limiting of the scope of the embodiments described herein, as other embodiments are within the scope of this disclosure. The elements and features shown in the drawings are not necessarily drawn to scale, emphasis instead being placed upon clearly illustrating the principles of the embodiments. Additionally, certain dimensions or positionings may be exaggerated to help visually convey certain principles. In the drawings, similar reference numerals between figures designate like or corresponding, but not necessarily the same, elements.

DETAILED DESCRIPTION

The embodiments described herein encode hydrogel structures with programmed morphologies and motions. The approach uses temperature-responsive hydrogel structures with photo-tunable, and thus locally programmable, degrees and rates of swelling and shrinking. The approach can be used to simultaneously print multiple 3D structures with custom designs from a single precursor solution in a one-step process. The process can print multiple 3D structures in a relatively short period of time, such as within 60 seconds, and is highly scalable. A number of versatile design rules are also presented for creating complex 3D structures, along with a dynamic theoretical model for predicting their motions. According to the results presented herein, the spatially non-uniform rates of swelling and shrinking of growth-induced 3D structures determine their dynamic shape changes. Shape-morphing 3D structures are demonstrated having diverse morphologies, including bioinspired structures with programmed sequential motions.

According to the embodiments described herein, spatially-controlled in-plane growth (e.g., expansion and contraction) of hydrogel sheets can be relied upon to form 3D structures via out-of-plane deformation (e.g., non-Euclidean plates). This approach defines 3D shapes with Gaussian curvatures, for example, thereby uniquely creating 3D structures with curved geometries.

Living organisms, ranging from plants to marine invertebrates, use similar approaches (e.g., differential growth) for fundamental biological processes, including morphogenesis, complex growth and movement, and adaptation to environments. By developing hydrogel structures having physical properties similar to those of soft tissues, the embodiments described herein have the potential to create 3D structures suitable for use in a number of different applications.

The manner or means with which to program dynamic growth-induced 3D motions remains largely unexplored. Previous theoretical and experimental studies have mainly focused on the formation of 3D shapes at equilibrium states, but their dynamic behavior at metastable states during shape transition is not well understood. A theoretical framework for predicting and programming dynamic shape changes is also unexplored. Furthermore, the principle has been demonstrated for relatively simple 3D shapes, mostly with axisymmetric geometries, but achieving non-axisymmetric 3D structures with complex morphologies presents theoretical and experimental challenges.

According to the embodiments described herein, digital light 4D printing (DL4P) can be relied upon to create dynamic 3D structures with programmed morphologies and motions. In that context, FIG. 1 illustrates an example of programming photo-tunable hydrogel structures to create 3D structures. FIG. 1 provides a representative illustration of the DL4P process. In the process, a precursor solution 10 of Poly(N-isopropylacrylamide) (pNIPAm), N,N'-methylene bisacrylamide (BIS)(as a short-chain crosslinker), and poly (ethylene glycol) diacrylate (PEGDA)(as a long-chain crosslinker) is prepared. The precursor solution 10 is introduced into a cell 20. This method can simultaneously print any number of hydrogel structures 40, each capable of forming different 3D shapes, from the single precursor solution in the cell 20. FIG. 1 illustrates the simultaneous printing of twelve hydrogel structures 40 in the cell 20.

Within the cell 20, the precursor solution 10 is exposed to light 30 through digital light projection grayscale lithography, for example, or another suitable technique. Based on the exposure to the light 30, any number of hydrogel structures 40 can be simultaneously printed with different growth functions $\Omega$ or patterns. The hydrogel structure 40 is one of 12 hydrogel structures simultaneously printed in the cell 20 and encoded with a growth function, $\Omega$. Thus, the hydrogel structure 40 is created from the exposure of the precursor solution 10 of Poly(N-isopropylacrylamide) (pNIPAm), N,N'-methylene bisacrylamide (BIS)(as a short-chain crosslinker), and poly(ethylene glycol) diacrylate (PEGDA) (as a long-chain crosslinker) with the light 30 through digital light projection grayscale lithography.

When the precursor solution 10 is exposed to light, the hydrogel structure 40 is formed to have spatially controlled polymer network densities. In FIG. 1, polymer network regions 42 and 44 of the hydrogel structure 40 are shown. The polymer network regions 42 and 44 are provided as representative examples formed by different light exposure time on the basis of varied spatial and temporal control of the light 30 through digital light projection grayscale lithography based on a growth function, $\Omega$ for a specific target 3D shape. The hydrogel structure 40 can include a continuity of regions including regions 42 and 44, among others, in practice. The region 42 was formed by a shorter light exposure time $t_{ex}$, and the region 44 was formed by a longer light exposure time tex. In the regions 42 and 44, links 50, 51, and 52 represent the pNIPAm, BIS, and PEGDA, respectively. As shown, the pNIPAm forms a lower density polymer network linked mostly by the PEGDA in region 42, and the pNIPAm from a higher density polymer network linked by both the BIS and the PEGDA in region 44.

As also shown in FIG. 1, the hydrogel structure 40 undergoes a reversible shape transition, between swelled and shrunk states, at about the temperature $T_c$. The temperature $T_c$ can vary depending upon the properties of the precursor solution 10 and other factors. An example value of $T_c$ is about ~32.5° C.

Homogeneous hydrogel disks with a diameter of 5 mm (i.e., hydrogel disks formed with constant $\Omega$) were prepared by the technique described in FIG. 1. The hydrogel disks were uniformly exposed to light over the entire disks with light exposure times of 8 to 70 s. The areas of the hydrogel disks at the swelled state $A_{25}$ were measured at 25° C. The areas of the hydrogel disks at the shrunk state $A_{35}$ were measured at 35° C. The areal swelling and shrinking ratios are defined as $A_{35}/A_0$ and $A_{25}/A_0$, respectively, where $A_0$ is the area of as-prepared hydrogel disks. The hydrogel disks were used to generate the calibration curves of the areal swelling and shrinking ratios versus light exposure time described below with reference to FIGS. 2A and 2B. This process induces essentially no or little variation of swelling and shrinking through the thickness and, thus, does not induce bending of homogeneous hydrogel disks.

The dynamic mechanical properties of the hydrogel structures at the swelled state were measured using a rheometer with a 20-mm plate geometry. Hydrogel disks with a diameter of 20 mm were used. The shear storage modulus G' and loss modulus G" were measured by frequency sweeps of 0.01 to 100 rad/s at an oscillatory strain of 1%. The hydrogel disks with a storage shear modulus larger than 20 Pa were used for the measurements of the swelling and shrinking ratios.

Further, the gel points of the hydrogel structures crosslinked with single crosslinkers were measured. Hydrogel disks with a diameter of 20 mm were prepared with single crosslinkers (BIS and PEGDA: 1 mol % of NIPAm in precursor solutions) with different light exposure times (BIS-crosslinked hydrogel structures: 4, 8, 12, and 16s; PEGDA-crosslinked hydrogel structures: 1, 2, 3, and 4s). The hydrogel disks that form stable hydrogel structures after washing with IPA were used for the measurements. The shear storage modulus G' and loss modulus G" were measured by frequency sweeps of 0.1 to 15 Hz at an oscillatory strain of 0.1% using the rheometer with a 20-mm plate geometry. To determine the gel points, tan $\delta$=G"/G' were plotted as a function of frequency. At the gel point, tan $\delta$=G"/G' has a constant value over the frequency sweep.

Figure 2A:
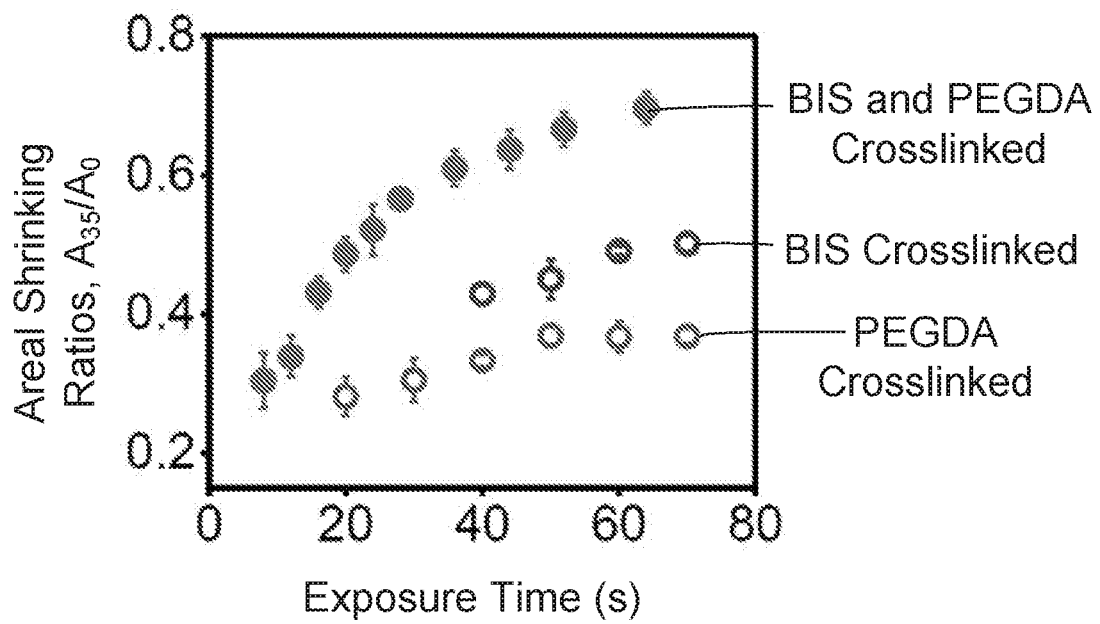
FIG. 2A illustrates areal shrinking ratios of hydrogel structures as a function of light exposure time according to various embodiments described herein.
Figure 2B:
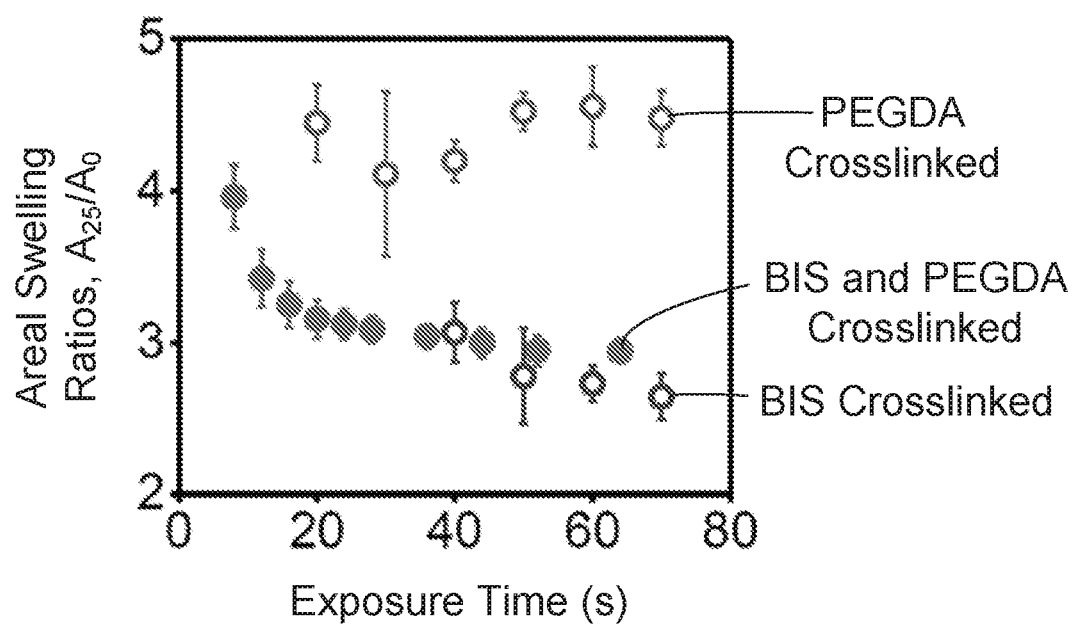
FIG. 2B illustrates areal swelling ratios of hydrogel structures as a function of light exposure time according to various embodiments described herein.
Figure 2C:
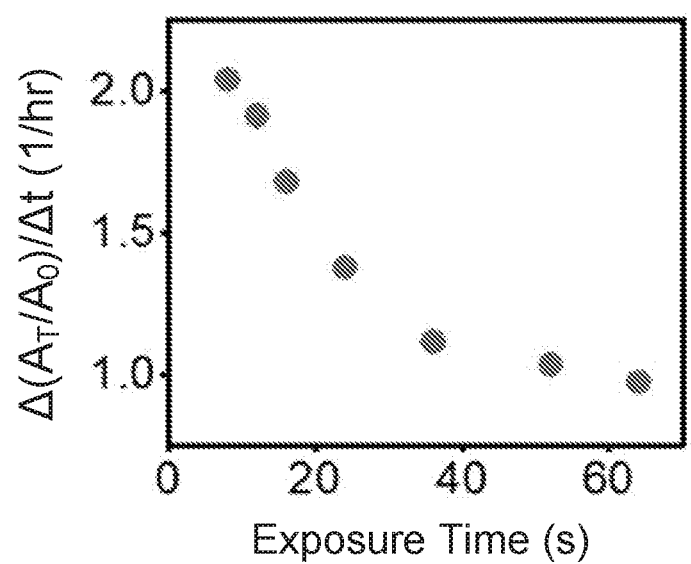
FIG. 2C illustrates areal swelling rates of hydrogel structures as a function of light exposure time according to various embodiments described herein.

FIG. 2A illustrates areal shrinking ratios of dual-, BIS-, and PEGDA-crosslinked pNIPAm hydrogel structures as a function of $t_{ex}$, and FIG. 2B illustrates areal swelling ratios of dual-, BIS-, and PEGDA-crosslinked pNIPAm hydrogel structures as a function of $t_{ex}$. The error bars indicate standard deviations for three independent measurements. FIG. 2C illustrates areal swelling rates of dual-crosslinked pNIPAm hydrogel structures as a function of $t_{ex}$.

The approach shown in FIG. 1 results in the formation of photo-tunable 2D hydrogel structures. The hydrogel structures can be encoded to have one or more spatially and temporally controlled growth (e.g., expansion and contraction) functions, $\Omega$, or target metrics in various regions. The controlled growth transforms the hydrogel structures into prescribed 3D structures and defines or programs the motions of the hydrogel structures.

Other studies have focused on 3D shapes at either swelled or shrunk states. As described herein, temperature-responsive hydrogel structures, having certain degrees and/or rates of swelling and shrinking, can be created to form certain 3D shapes at both the swelled and shrunk states. In particular, the ability to control the rates uniquely among different regions in the hydrogel structures enables a new strategy for programming growth-induced 3D motions. The method can simultaneously print multiple 3D structures with custom designs and sizes, using digital light projection grayscale lithography, for example, from a single bath of precursor solution. The method can be performed relatively quickly and is highly scalable.

As described in additional detail below, taking advantage of photo-tunable hydrogel structures and the flexible 2D printing method for 3D material programming (e.g., without the need for multiple physical masks or nozzles), a set of simple and versatile design rules are developed. The concept of modularity is also introduced for creating complex 3D structures with diverse morphologies, including ray-inspired structures with programmed motions. To investigate the dynamic growth-induced motions, the concept of dynamic target metrics is also used to develop a dynamic theoretical model. Experimental and theoretical studies reveal that the spatially non-uniform rates of swelling and shrinking of growth-induced 3D structures determine their dynamic shape changes. Furthermore, the swelling and shrinking rates of the hydrogel structures are photo-tunable and thus locally programmable. The ability to spatially control the rates of shape change leads to the ability to fabricate dynamic 3D structures with programmed sequential motions.

The DL4P approach described herein relies on the ability to prepare temperature-responsive hydrogel structures with varying compositions and material properties (e.g., degrees and rates of swelling and shrinking) from a single precursor solution through photopolymerization and crosslinking. The modulation of the material properties of the hydrogel structures is based on control of the polymerization and crosslinking reactions in the hydrogel structures. Control of the polymerization and crosslinking reactions is achieved through the use of two types of crosslinkers of different lengths and the use of either shorter or longer exposure times $t_{ex}$. The phototunability provides a flexible means to encode the hydrogel structures with spatially and temporally controlled growth, which can be used to program the formation of 3D structures and their motions.

In one example, the precursor solution consists of N-isopropylacrylamide (NIPAm), N,N'-methylene bisacrylamide (BIS, a short-chain crosslinker), and poly(ethylene glycol) diacrylate (PEGDA, a long-chain crosslinker). For an equimolar concentration of crosslinkers, crosslinking with PEGDA forms gels faster than with BIS, due to longer distances between the crosslinking points of PEGDA. The BIS- and PEGDA-crosslinked hydrogel structures swell and shrink in different degrees as shown in FIG. 1.

Thus, pNIPAm hydrogel structures crosslinked with both BIS and PEGDA have a larger photo-tunable range of swelling and shrinkage over a wider range of $t_{ex}$ than those crosslinked with single crosslinkers. The dual crosslinking increases the range of $t_{ex}$ that can be used to tune the shrinking and swelling ratios. Crosslinking with long-chain crosslinkers (e.g., PEGDA) forms a low density hydrogel framework at an early stage (low monomer conversion), as shown in the region 52 in FIG. 1. On the other hand, the conversion of monomers to polymers and their crosslinking via short-chain crosslinkers (e.g., BIS) occurs within the hydrogel throughout the time course of photopolymerization, increasing the density of the polymer networks, as shown in the region 51 in FIG. 1. Moreover, crosslinking via PEGDA is expected to be suppressed at the late stage because of diffusional limitations in high-density polymer networks. This mechanism was verified by measuring the density of the polymer networks as a function of $t_{ex}$. The density increases with $t_{ex}$. The increase in the density, in turn, reduces the degrees and rates of macroscopic swelling and shrinking. This mechanism differs from other known mechanisms by crosslink density control through tailored light irradiation, which, for example, tunes the swelling of the resulting hydrogel structure.

To validate the DL4P approach and demonstrate its accuracy, well-defined geometric 3D structures with axisymmetric metrics were developed. In that context, FIG. 3A illustrates shape-morphing 3D structures with axisymmetric metrics developed according to various embodiments described herein. FIG. 3A illustrates 3D structures with constant Gaussian curvatures, K, at the shrunk state and the corresponding structures at the swelled state, including spherical cap, saddle, and cone shapes, from top to bottom. FIG. 3B illustrates reconstructed 3D images of the experimental, swelled structures shown in FIG. 3A, along with the theoretical shapes of the spherical cap, saddle, and cone shapes from FIG. 3A. FIG. 3A also illustrates scale bars in the shrunk and swelled states.

As shown in FIG. 3A, the embodiments described herein can define target 3D shapes at both the swelled ($\Omega$>1) and the shrunk ($\Omega$<1) states. The equilibrium 3D shape is selected from the competition between bending ($E_B \sim t_h^3$, where $t_h$ is the thickness of a sheet) and stretching ($E_S \sim t_h$) energies. As the thickness decreases, the hydrogel sheet converges to the stretch-free configuration that fully follows the target metric. However, the actual metric adopted by experimental 3D structures differs from the target metric, because of a finite-thickness bending energy. The structure at the shrunk state can thus yield a 3D shape closer to the theoretical configuration described by the target metric than one at the swelled state. In addition, the use of hydrogel structures at the shrunk state is beneficial for practical applications, for example, because of their enhanced mechanical properties and the formation of target shapes under physiological conditions (T=37° C.) for potential biomedical applications. Thus, structures can be designed with areal growth functions, $\Omega$, for target shapes at the shrunk state.

In FIG. 3A, the spherical cap, saddle, and cone structures were formed with constant Gaussian curvatures of K>0, K<0, and K=0, respectively. These structures were formed by encoding hydrogel structures at 400 μm in thickness with areal growth functions $\Omega = c/(1+(r/R)^2)^2$ for the spherical cap with $K=4/(cR^2)$, $\Omega = c/(1-(r/R)^2)^2$ for the saddle shape with $K=-4/(cR^2)$, and $\Omega = c(r/R)^{2(\alpha-1)}$ for the cone with K=0, where r is the radial position and c, R, and a are constants. Digital light projection grayscale lithography was used for hydrogel programming. The growth functions were derived from the target shapes based on the Theoretical Models in Notes 1-3 described below. The resulting structures agree quantitatively with the theoretical structures, as shown in FIG. 3B, reflecting the accuracy of the approach. For example, the experimentally measured K of the spherical cap and saddle structures are 0.0464 mm$^{-2}$ and −0.0727 mm$^{-2}$, which match well with the theoretically calculated K of 0.0468 mm$^{-2}$ and −0.0722 mm$^{-2}$, respectively.

Figure 4A:
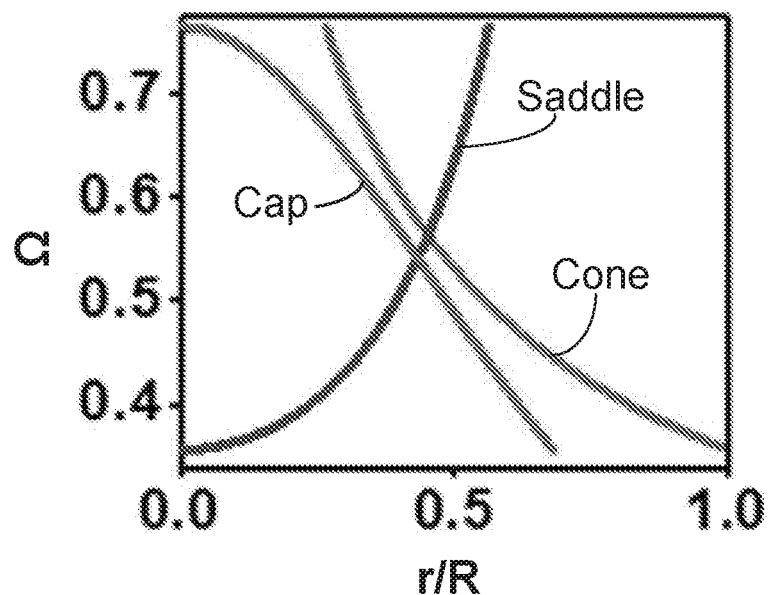
FIG. 4A illustrates the growth patterns or functions used to form the structures in FIG. 3A according to various embodiments described herein.
Figure 4B:
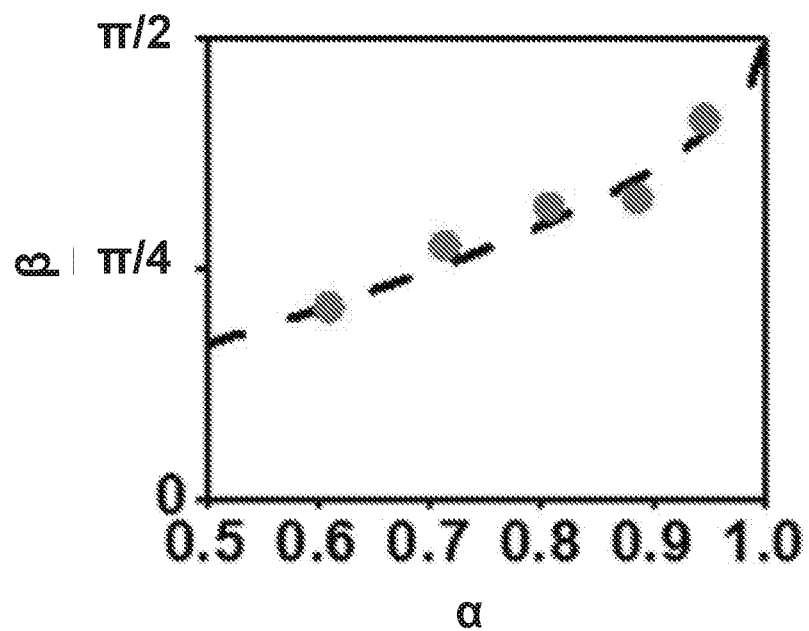
FIG. 4B illustrates experimental and theoretical values of the vertex angle of the cone structure shown in FIG. 3A for different a according to various embodiments described herein.

Additionally, FIG. 4A illustrates the $\Omega$ used to form the structures shown in FIG. 3A, and FIG. 4B illustrates experimental (solid circles) and theoretical (dashed line) values of β with different a in $\Omega$ for the cone structures shown in FIG. 3A. The cone structures constructed with different exponents a have the programmed value of the vertex angle β (β=sin$^{-1}$α) as shown in FIG. 4B and described in Note 3.

Note 1: Theoretical Model

The theoretical model is based on the theory of differential geometry of surfaces and the concept of target metrics (e.g., non-Euclidean plates). A differential growth (e.g., swelling or shrinking)-induced 3D shape or surface adopts an isotropic embedding of a target metric. The metric encodes the local equilibrium distances between points on the 3D shape or surface. Because bending ($E_B \sim t_h^3$, where $t_h$ is the thickness of a sheet) is energetically less costly than stretching ($E_S \sim t_h$) in a thin sheet, the internal stresses developed by non-uniform in-plane growth are released by out-of-plane bending deformation ($E_B < E_S$). As the thickness of the sheet decreases, the shape converges to the embedding of the lowest bending energy.

Consider a 3D shape (surface) with the parameterization:

$$x(u, v) = (x_1(u, v), x_2(u, v), x_3(u, v)), \quad (S1)$$

where (u, v) are points on the 2D plane. The square of the element of arc length, or the distance between neighboring points, in the 3D surface is given by the first fundamental form (or the metric):

$$ds^2 = Edu^2 + 2Fdudv + Gdv^2, \quad (S2)$$

where E, F, and G are the coefficients of the first fundamental form. Further, assume that a spatially-controlled in-plane growth (e.g., swelling or shrinking) of a 2D plane in a coordinate system (u', v') can induce the formation of the 3D shape via out-of-plane deformation. The square of the distance between points on the 2D plane before deformation is:

$$dl^2 = g du' dv', \quad (S3)$$

where g is the metric (or first fundamental form) of the 2D plane before deformation. The spatially controlled growth determines new equilibrium distances between points on the 2D plane. The information of the new distances is contained in a new metric $\bar{g}$. To form the 3D shape with the growth, the new metric of the 2D plane should be the same as that of the 3D shape:

$$ds^2 = \bar{g} du' dv'. \quad (S4)$$

The new metric $\bar{g}$ is defined as the target metric. If the target metric (or the parameterization) is isothermal (or conformal), which is the case for the material systems (E=G and F=0), the target metric with scale function λ can be written as:

$$\bar{g} = \lambda^2 g, \quad (S5)$$

where $\lambda^2 = \Omega$. $\Omega$ is defined as the areal growth function. $\Omega$ contains all the information about how to encode a 2D plane with spatially controlled growth to form the target 3D shape. According to Gauss's *Theorema egregium*, the Gaussian curvature is then:

$$K = -\Delta(\ln\lambda)/\lambda^2 = -\Delta(\ln\Omega)/(2\Omega), \quad (S6)$$

where Δ is the Laplacian.

Note 2: Theoretical Model for Axisymmetric 3D Structures

An axisymmetric 3D shape (surface of revolution) is also considered in a cylindrical coordinate system (ρ, φ, z), where the z axis is the axis of symmetry (axis of rotation) and z=f(ρ). Then, the square of the element of arc length on the 3D shape can be found from Equation S2: $ds^2 = (1+f_\rho^2)d\rho^2 + \rho^2 d\varphi^2$, where $f_\rho = df/d\rho$. The 3D shape can be induced by encoding a 2D plane with a growth function $\Omega$ in a polar coordinate system (r, θ). Then, the following equation can be determined from Equation S4:

$$(1+f_\rho^2)d\rho^2 + \rho^2 d\varphi^2 = \Omega(r)(dr^2 + r^2 d\theta^2). \quad (S7)$$

The left side of Equation S7 represents the distance between two neighboring points on the 3D shape, whereas the right side represents the distance between neighboring points on the 2D plane after growth. In other words, Equation S7 describes how the spatially-controlled growth of the 2D plane (right side) induces the 3D shape (left side). Because the growth is axisymmetric, it is assumed that the angle between neighboring points on the 2D plane does not change during growth and, thus, obtain dφ=dθ and $\rho^2 d\varphi^2 = \Omega(r) r^2 d\theta^2$. Then, Equation S7 gives:

$$\rho^2 = \Omega(r) r^2, \text{ and} \quad (S8)$$

$$(1+f_\rho^2)d\rho^2 = \Omega(r) dr^2. \quad (S9)$$

For a given axisymmetric 3D shape, the relationship of r and ρ and that of $\Omega$ and ρ can be determined. For a given $\Omega$, the 3D shape that adopts $\Omega$ using Equations S8 and S9 can be predicted.

Note 3: The Determination of the Growth Function (Target Metric) for a Target 3D Structure for Axisymmetric 3D Structures The growth function $\Omega$ for a spherical cap can also be determined. A spherical cap with a radius of $r_0$ is given by:

$$\rho^2 + (z-z_0)^2 = r_0^2, \tag{S10}$$

where $z_0$ is a constant. The, $\rho$ and $\Omega$ can be determined as a function of r using Equations S8, S9, and S10, as follows:

$$\rho = \frac{2r_0(r/R)}{1+(r/R)^2}, \text{ and} \tag{S11}$$

$$\Omega = \frac{c}{\left(1+(r/R)^2\right)^2} \tag{S12}$$

where $c = 4(r_0/R)^2$. The local Gaussian curvature $K = 1/r_0^2 = 4/(cR^2)$ can be found using Equations S6 and S12. Equation S12 can be used to experimetally create a spherical cap at the shrunk state and Equation S10 can be used to construct a theoretical 3D structure and K.

$\Omega$ can also be determined for a cone structure. A cone with a vertex angle of $2\beta$ is given by:

$$z - Z_0 = \rho \cot \beta. \tag{S13}$$

The values of $\rho$ and $\Omega$ can be determined as a function of r using Equations S8, S9, and S13, as follows:

$$\rho = \rho_0 \left(\frac{r}{R}\right)^\alpha, \tag{S14}$$

where R is a constant and exponent $\alpha = \sin \beta$, and $$\Omega = c\left(\frac{r}{R}\right)^{2(\alpha-1)}, \tag{S15}$$

where $c = (\rho_0/R)^2$. $K=0$ can be obtained using Equations S6 and S15. Equation S15 can also be used to experimetally create a cone structure with a vertex angle of $2\beta$ at the shrunk state, and Equation S13 can be used to construct a theoretical 3D structure and K, respectively.

For a saddle shape, it is possible to use:

$$\Omega = \frac{c}{\left(1-(r/R)^2\right)^2}. \tag{S16}$$

It is then possible to obtain $K = -4/(cR^2)$ using Equations S6 and S16. Equation S16 can also be used to experimentally create a saddle structure. A theoretical 3D structure with constant negative K can also be constructed by introducing two principle curvatures $[k_1 = -k_2 = 2/(\sqrt{c}R)]$ into a flat surface.

Axisymmetric shapes of cap and cone with different amounts of programmed radius and deficit angles ($\delta$) were also made to study the accuracy of the method with respect to the overall sample sizes. The cap samples were printed using Equation S17 at different R values of 3, 5, 7, 9, and 10 mm.

$$\Omega(r/R) = \frac{\Omega_{max}}{\left(1+(r/R)^2\right)^2} \tag{S17}$$

$$0 < r/R < \sqrt{\sqrt{\Omega_{max}/\Omega_{min}} - 1} \tag{S18}$$

In which $\Omega_{max}$ and $\Omega_{min}$ are maximum and minimum achievable arial desweleing rates, respectively, and r/R is normalized printing calendrical coordinate.

Cone samples were also made through Equation S19 at different a values of 0.5, 0.6, 0.7, 0.8, 0.9.

$$\Omega_{cone}^i = \Omega_{min}\left(\frac{r}{R}\right)^{2(\alpha_i - 1)} \tag{S19}$$

The half-vertex angle ($\beta$) and angular deficit ($\delta$) can be expressed as:

$$\beta = \text{ArcSin}(\alpha) \tag{S20}$$

$$\delta = 2\pi(1-\alpha) \tag{S21}$$

Scanning electron microscope (SEM) images where used to study the surface finish of the structures. A microhardness test also was performed on dried samples at the load of 0.1 KgF. The hardness in Vickers (HV) was calculated as follows:

$$HV = 0.1891 \frac{F}{d^2} \tag{S22}$$

Figure 5A:
FIG. 5A illustrates a structure formed as an Enneper's minimal surface according to various embodiments described herein.
Figure 5B:
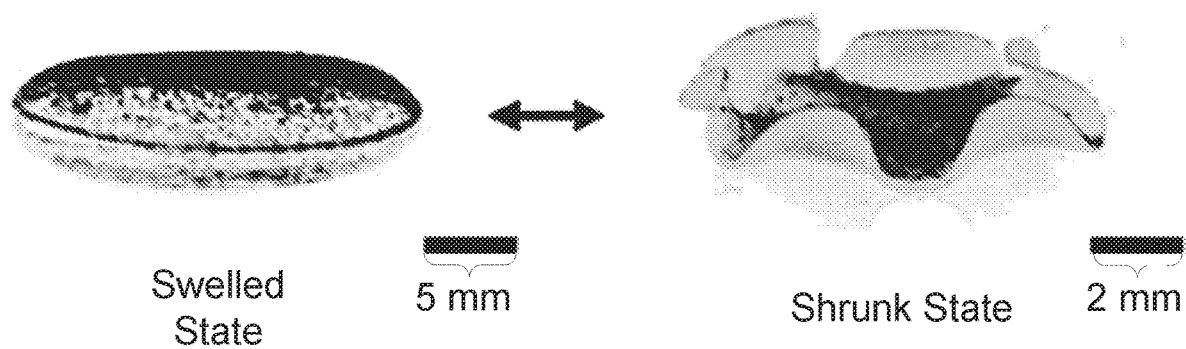
FIG. 5B illustrates another structure formed as an Enneper's minimal surface according to various embodiments described herein.
Figure 5C:
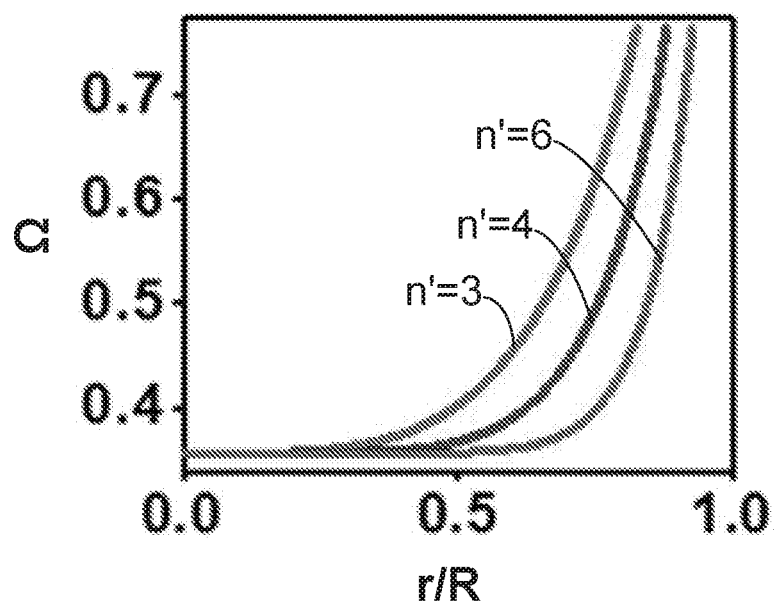
FIG. 5C illustrates the growth functions used to form the Enneper's minimal surfaces shown in FIGS. 5A and 5B, among others, according to various embodiments described herein.

The approach described herein was also verified by creating Enneper's minimal surfaces. FIGS. 5A and 5B illustrate structures formed as Enneper's minimal surfaces according to various embodiments described herein. The structures were formed using $\Omega(r) = c[1+(r/R)^{2(n'-1)}]2$. As expected, the growth functions with different wrinkles, n', induce Enneper's surfaces with the targeted number of wrinkles n'. FIG. 5A illustrates a structure with 4 wrinkles, and FIG. 5B illustrates a structure with 6 wrinkles. FIG. 5C illustrates the growth functions used to form the Enneper's minimal surfaces shown in FIGS. 5A and 5B, among others.

As shown in FIG. 5B, the structures reversibly transform between prescribed 3D shapes at the swelled and shrunk states in response to temperature change. The 3D structures at the swelled state adopt new metrics, determined by the areal swelling ratios and the growth functions designed for the target shapes at the shrunk state. Because of the inverse relationship between the areal swelling and shrinking ratios, 3D shapes with K>0 at the shrunk state generally transform to 3D shapes with K<0 at the swelled state and vice versa.

The methods described herein can be relied upon to create structures of other shapes. For example, structures similar to the cap structure shown in FIG. 3A, but with a smooth gradient in Gaussian curvature, K, can be formed. Other design rules for creating non-axisymmetric 3D structures with diverse morphologies can also be established. For example, structures can be created with different growth functions combined radially and azimuthally. Additionally, structures can be created with a number of nodes, along $\theta$, of alternating Gaussian curvatures.

Thus, the embodiments can involve the combination and transformation of target metrics and the concept of modularity. As implemented in the metric space, these schemes require new design rules for how to interface metrics. Thus, the concepts of linkers and transitional components at the interfaces of metrics are introduced. The radial and azimuthal combinations of growth functions yield hybrid 3D structures with alternating features of the functions along the r and θ directions, respectively. For example, the radial combination of $\Omega_1$ for a spherical cap and $\Omega_2$ for a saddle induces a structure with K>0 and K<0 in the central and outer regions, respectively. Another example is a hybrid structure that combines a spherical cap and a cone. The azimuthal combination of two functions, for example, $\Omega_1$ (5°<θ<85° and 185°<θ<265°) and $\Omega_2$ (95°<θ<175° and 275°<θ<355°), yields a structure with alternating features of $\Omega_1$ and $\Omega_2$ along θ. A linear linker with a form $\Omega_L=(\Omega_1-\Omega_2)\theta/\Delta\theta+\Omega_2$ with Δθ=10° at the interfaces of $\Omega_1$ and $\Omega_2$ can also be introduced to make Ω continuous, as sharp discontinuities in Ω can cause stress accumulation and thereby shape distortion.

Transforming axisymmetric Ω into a function of θ in the form $\Omega(r, \theta)=c(\theta)\Omega(r/(\alpha(\theta)R))$ leads to non-axisymmetric structures with varying morphologies along θ. c(θ) scales Ω along θ. Therefore, transforming $\Omega(r)=c(r/R)^2+\Omega_{min}$ for a modified excess cone with $c(\theta)=c_0 \cos^2(L\theta)$, where L is a constant, forms a shape with alternating K>0 and K<0 and a programmed number of nodes n'=2 L.

As another example, elongated saddle structures can be created. The directions of the principal curvatures at the center of the saddle structure can align with the major and minor axes of the ellipse, suggesting that this configuration is an embedding of the lowest bending energy of the target metric. Furthermore, adding periodicity into Ω with $\alpha(\theta)=\sqrt{1+(b^2-1)\sin^2 L\theta}$ modulates the number of nodes n'=2 L along θ. Using this transformation, spherical cap and saddle-like structures can be formed with a targeted number of legs. These examples demonstrate the versatility of the embodiments in creating diverse 3D morphologies.

Figure 6:
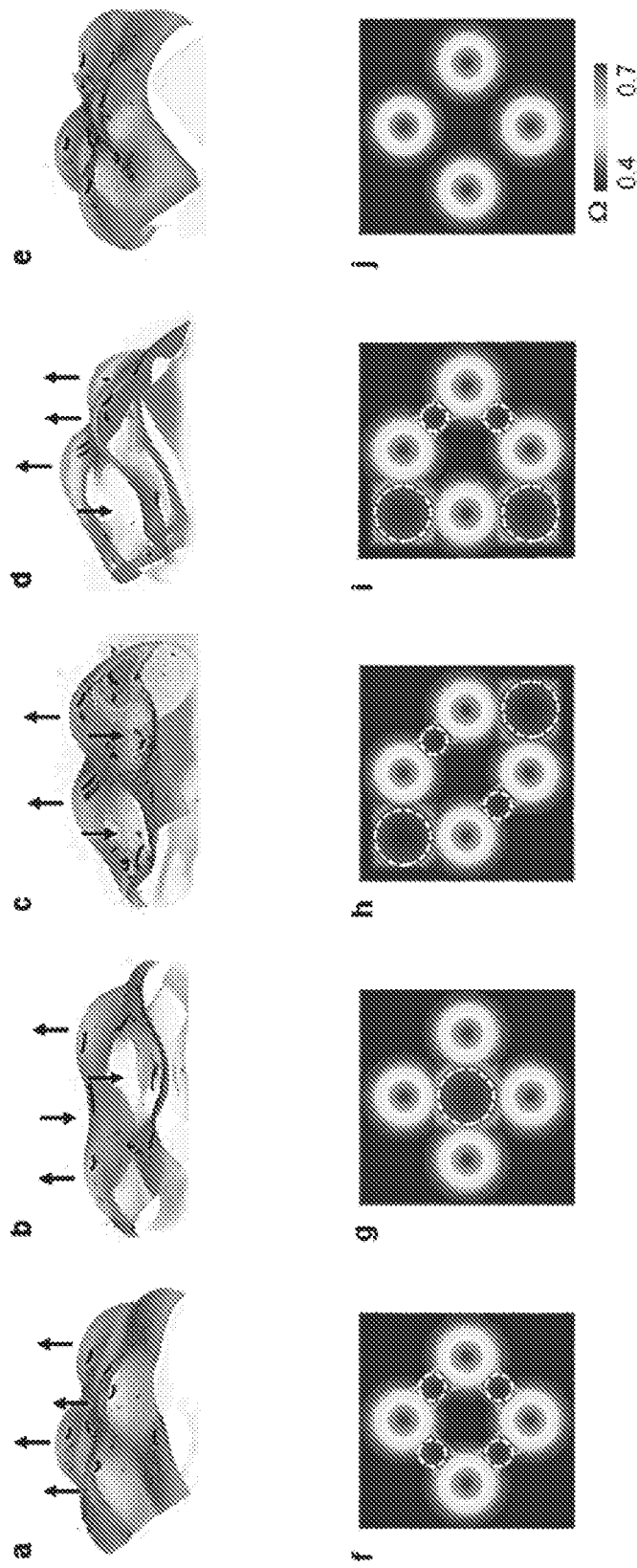
FIG. 6 illustrates a number of multi-modular 3D structures with directional control, where the modules are programmed to deform in the directions indicated by the arrows, developed according to various embodiments described herein.

The structures discussed above can be further used as building blocks for multi-modular 3D structures. In that context, FIG. 6 illustrates a number of multi-modular 3D structures according to various embodiments described herein. In (a)-(e), FIG. 6 illustrates examples of multi-modular 3D structures with four modules. The modular assembly of target metrics can create 3D structures with broad morphological and functional diversity. However, there may be an intrinsic problem resulting from the assembly of modules in the metric space. Each module can randomly adopt the direction of deformation (e.g., upward or downward) or the orientation with respect to other modules due to the symmetric nature of metrics. Thus, a multi-modular Ω can generally form multiple different conformations presumably with the same elastic energy.

To tackle this problem, the concept of transitional components is introduced, designed to control the direction of deformation and the orientation of modular components. A saddle-like structure with K<0 has the principle curvatures with the same sign along its parallel edges. It was postulated that modular components with K>0 that share the parallel edges of a saddle-like structure (K<0), or a parallel transitional component (e.g., the small dotted circles in FIG. 4), would deform in the same direction as the parallel edges.

On the other hand, modular components with K>0 that share the perpendicular edges of a saddle-like structure (K<0), or a perpendicular transitional component (e.g., the large dotted circles in FIG. 4), would deform in the opposite directions. Thus, the structures shown in (a)-(d) of FIG. 6 have directional control, and the structure shown in (e) does not have directional control. The structures were programmed to deform in the directions indicated by the arrows. In (f)-(j), the strategies used to control the orientation of the modules in the corresponding structures shown in (a)-(e), respectively, are shown. That is, the maps in (f)-(j) illustrate the growth functions Ω used to create the structures shown in (a)-(e). The small and large dotted line circles indicate the parallel and perpendicular transitional components, respectively. Placing the parallel and perpendicular transitional components between the modules (indicated by the small and large circles, respectively) led to multi-modular structures with designed morphologies. In contrast, the modules in a control structure without transitional components tend to deform in the same direction, implying slight variations in shrinkage through the thickness. The variations make a specific direction energetically favorable for all modules, as is exhibited in (e) of FIG. 4.

The design rules offer simple yet versatile ways to build complex 3D structures without the need for extensive computation. To demonstrate this capability, a number of ray-inspired 3D structures were formed. The structures replicate the key morphological features of stingrays, including the pectoral fins with K<0. FIG. 7 illustrates a 3D structure developed based on a stingray model according to various embodiments described herein. The modules for the body and the pectoral fins were designed based on the K map shown. FIG. 7 also shows stingray-inspired motions of the 3D structures. The arrows indicate the direction of the motions.

The growth functions for the body and the pectoral fins were designed and merged with linear linkers, using the design rules described above For example, the module for the body structure with the linkers was used as a transitional component that controls the orientation of the left and right pectoral fins with respect to the body and, thus, synchronizes their motions. Furthermore, the ray-inspired structures were designed to produce different types of oscillatory flapping motions in response to temperature cycles (e.g., between 31.5° C. and 33.5° C.), mimicking those of stingrays.

Figure 8:
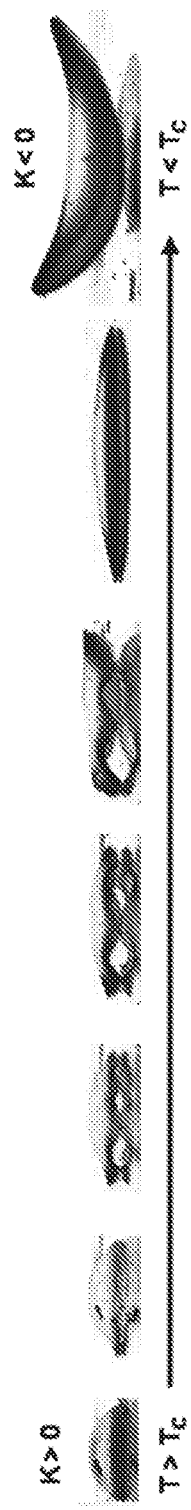
FIG. 8 illustrates the dynamic behavior of growth-induced 3D structures according to various embodiments described herein.
Figure 9:
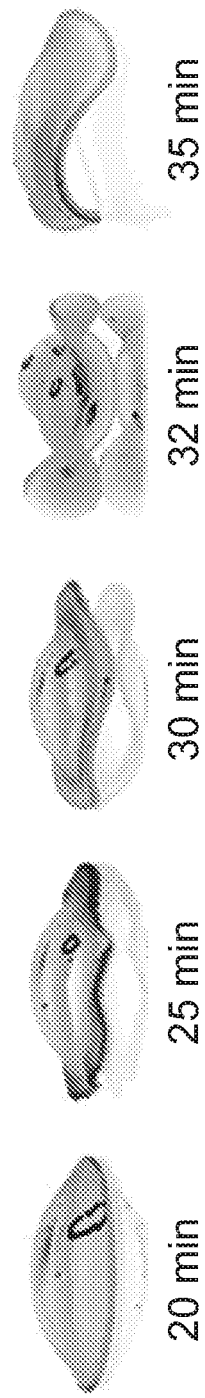
FIG. 9 also illustrates the structures that replicate the dynamic behavior of growth-induced 3D structures shown in FIG. 8 according to various embodiments described herein.

The manner in which growth-induced 3D structures transform their shapes was also investigated. In that context, FIGS. 8 and 9 illustrate the dynamic behavior of growth-induced 3D structures according to various embodiments described herein. FIG. 8 illustrates the shape evolution of a spherical cap during cooling. Despite the simple shapes of the spherical cap at equilibrium (swelled and shrunk states), the structure undergoes complex shape transformations. To elucidate how it changes into complex intermediate shapes, the dynamic behaviors of homogeneous hydrogel structures were quantified. The measurements indicate that the swelling rates decrease with $t_{ex}$, reflecting the difference in the rate of diffusion of water through the hydrogel structures with different densities. The crossover of $A_T/A_0$ of hydrogel structures prepared with short and long $t_{ex}$ at 20 to 40 min implies how growth-induced structures transform between shapes with K>0 and K<0.

Experimental and theoretical results reveal that the spatially non-uniform rates of swelling and shrinking of growth-induced 3D structures determine their dynamic shape changes at metastable states. To verify this mechanism and predict the dynamic shape evolution, the concept of dynamic target metrics is introduced. To that end, swelling and shrinking ratios, $A_T/A_0$, can be constructed as a function of $t_{ex}$ at times t, analogous to the static calibration curves shown in FIGS. 2A and 2B. The dynamic calibration curves show how the local areas created with $t_{ex}$ in 3D structures swell (or shrink) with t.

The dynamic growth functions $\Omega_t$ for the spherical cap from its static growth function were also determined using the dynamic calibration curves. From this information, $\Omega_t$ shows how the metric of the spherical cap and thus its shape transform from elliptic (K>0) to hyperbolic (K<0) forms. During this transition, the growth function undergoes complex transformations, forming hybrid elliptic and hyperbolic metrics and thus hybrid 3D shapes.

The spatially non-uniform kinetics of swelling produces hybrid $\Omega_t$ with a minimum at (r/R)min at t of 20 to 40 min. The functional form of $\Omega_t$ (e.g., sharp change in the gradient of $\Omega_t$ at r/R>(r/R)$_{min}$) reflects how $\Omega_t$ form complex 3D morphologies with wrinkles, reminiscent of Enneper's surfaces. $\Omega_t$ at r/R<(r/R)$_{min}$ and r/R>(r/R)min represent the spherical cap-like shape in the center and the wrinkles in the edge, respectively. The shift of (r/R)min from the edge toward the center results in the increase in the amplitude and wavelength of wrinkles and the decrease in their number and the region of the spherical cap-like shape in the center. The spherical cap-like shape in the center gradually disappears with time (from around 40 min). The dynamic K maps theoretically calculated from $\Omega_t$ reflect the experimentally observed shape transformations.

To further demonstrate that $\Omega_t$ can predict the dynamic behavior, the dynamic shapes of the spherical cap were replicated using $\Omega_t$. Because the range of $\Omega_t$ is not accessible by the material systems, $\Omega_t$ was rescaled to the full range of experimentally accessible $\Omega$. The replicated structures reproduce the key signatures of the shape evolution, as shown in FIG. 9, including the formation of wrinkles and their shape changes (e.g., increase in the amplitude and wavelength of the wrinkles, decrease in the number of wrinkles, and gradual disappearance of the spherical cap-like shape in the center). The discrepancy in the detailed shapes (e.g., enhanced wrinkles) is attributed to the use of normalized $\Omega_t$. Moreover, this approach that uses $\Omega_t$ for 3D shaping provides new pathways for creating complex 3D structures. This approach offers rich sources to design complex 3D structures, difficult to access with current theories (e.g., wrinkle formation), and to understand how differential in-plane growth translates to 3D shapes. Manufacturing complex 3D structures, such as those shown in FIG. 9, is difficult and expensive to achieve by other methods.

Another important finding is that the swelling and shrinking rates of the hydrogel structures are photo-tunable and thus locally programmable. To demonstrate the ability to control the speed of shape change, saddle structures were created with an identical shape but different speeds of shape transformations. To create these structures, $\Omega_{fast}$ and $\Omega_{slow}$ were designed with the same functional form ($\Omega$ for a saddle shape) but in different ranges. As designed, the structure with $\Omega_{fast}$ transforms its shape faster than the structure with $\Omega_{slow}$. The dynamic K maps theoretically calculated from the dynamic growth functions describe the experimentally observed shape transformations with different speeds. Within the structures, due to the difference in the range of $\Omega$, the central regions (r/R~0; low range $\Omega$) transform faster than the edge regions (r/R~0.4; high range $\Omega$). The same trend can be observed in the spherical cap structure, in which the edge region (low range $\Omega$) transforms faster than the central region (high range $\Omega$).

The ability to spatially control the rate of shape transformation permits the creation of dynamic 3D structures with programmed sequential motions, which are difficult to achieve with global external stimuli. To demonstrate this, a ray-inspired 3D structure with programmed sequential motions was fabricated. The structure consists of modules for the body (K>0), front wings (K<0), and rear wings (K<0). The front and rear wings were designed to transform fast and slowly, respectively, and thereby be sequentially actuated in response to temperature change. As designed, the front wings transform first from a shape with $K_c$<0 to $K_c$>0 (around 5 min), gradually lifting the rear wings, while the rear wings slowly transform (e.g., $K_c$<0 up to 10 min) and flap after 20 min. Moreover, it is possible to control the oscillatory motions (e.g., amplitude and frequency) by modulating temperature cycles.

The approach described herein uses the spatially and temporally controlled growth for programming 3D shapes and their motions, possibly with an unlimited number of degrees of freedom, could thus create dynamic 3D structures with complex morphologies and motions. The ability to program growth-induced 3D shapes and motions could transform the way engineering systems, such as robots, actuators, and artificial muscles, are designed. The concept is applicable to other programmable materials. The 2D printing approach for 3D material programming represents a scalable and customizable 3D manufacturing technology, and it can be integrated with existing 2D fabrication methods and devices for multi-functionalities and broader applications.

Figure 10:
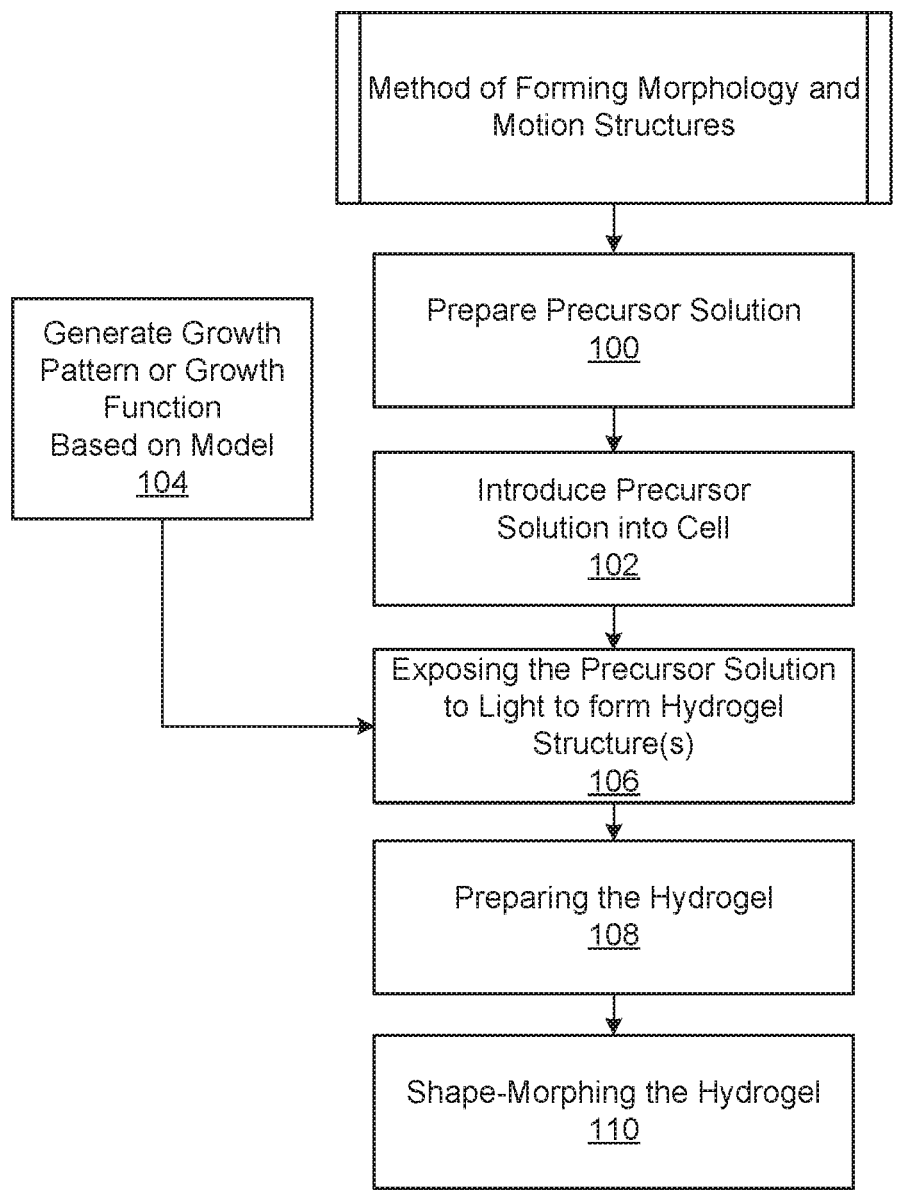
FIG. 10 illustrates a process for forming morphology and motion structures according to various embodiments described herein.

Turning to FIG. 10, a process is described for forming morphology and motion structures according to various embodiments described herein. At step 100, the process includes preparing a precursor solution. For example, precursor solutions for pNIPAm crosslinked with BIS and PEGDA can be prepared by dissolving N-isopropylacrylamide (NIPAm) (0.4 g), N,N'-methylene bisacrylamide (BIS) (0.5 mol % of NIPAm), poly(ethylene glycol) diacrylate (PEGDA) with an average molecular weight (MW) of ~700 g/mol (0.125 mol % of NIPAm), and diphenyl(2,4,6-trimethylbenzoyl)phosphine oxide (PBPO) (0.15 mol % of NIPAm) in 1 mL aqueous solutions (1:3 ratio of water and acetone by volume). However, other precursor solution ratios of the pNIPAm, BIS, PEGDA, and aqueous solutions can be relied upon.

Additionally, precursor solutions for pNIPAm crosslinked with BIS can be prepared by dissolving NIPAm (0.2 g), BIS (0.25 to 5.0 mol % of NIPAm), and PBPO (0.3 mol % of NIPAm) in 1 mL aqueous solutions (1:3 ratio of water and acetone). Further, precursor solutions for pNIPAm crosslinked with PEGDA were prepared by dissolving NIPAm (0.2 g), PEGDA (1.0 to 10.0 mol % of NIPAm), and PBPO (0.3 mol % of NIPAm) in 1 mL aqueous solutions (1:3 ratio of water and acetone).

In other embodiments described in further detail below, other materials can be added to the precursor solutions, including silica, gold, ceramic, etc., in the form of powder or other form, to achieve solid polymer matrix composites with desired 3D shapes.

At step 102, the process includes introducing the precursor solution into a cell. Here, a cell for projection lithography can be prepared by placing a polydimethylsiloxane (PDMS) spacer on a PDMS substrate. The PDMS spacer can have a thickness of 400 μm in one example, although other thicknesses can be relied upon. After purging the precursor solution prepared at step 100 with nitrogen to reduce the effects of oxygen on photopolymerization, the precursor solution can be introduced into the cell. The cell can then be covered with a glass coverslip (e.g., 150 μm in thickness).

After step 102, the precursor solution is ready for exposure to light through dynamic light projection grayscale lithography, for example, to form hydrogel structures. The control for this exposure, however, is determined separately at step 104. Particularly, at step 104, the process includes generating one or more growth patterns or functions $\Omega$ to direct the dynamic light projection grayscale lithography (e.g., the exposure pattern). The growth patterns or functions Ω can be determined according to any of the models described herein depending upon the desired shape of the structure or structures being designed, the morphologies of those structures, and the potential motions of those structures.

Generally, the growth patterns can be determined for 3D structures using the models described herein, which, in some cases, can be implemented using automated software tools, such as MATLAB®, 3DS MAX®, or other suitable tools. For example, growth functions Ω designed for target 3D shapes were converted into 2D maps of light exposure times using calibration curves of areal swelling and shrinking ratios versus light exposure time, such as those described herein, with MATLAB® code. The growth functions can define local $A_T/A_0$ of 2D structures, for example. Stereolithography (STL) files can be generated, containing the information of the 2D maps of light exposure times for use in later process steps At step 106, the process includes exposing the precursor solution in the cell with light to form one or more hydrogel structures. The precursor solution can be exposed with light by dynamic light projection grayscale lithography using a digital light processing (DLP) projector. Here, the precursor solutions can be exposed with spatially and temporally controlled light from the DLP projector, which may include light in the visible (VIS) to ultraviolet (UV) range, based on the growth patterns or growth functions Ω generated at step 104. Due to the light, the precursor solutions can be polymerized and crosslinked into number of hydrogel structures, by spatially and temporally controlling the light applied to the cell according to the STL files generated at step 104. The hydrogel structures that form the same or different shapes can be printed simultaneously in the cell.

At step 108, the process includes preparing the hydrogel structures formed at step 106. Preparing can include a number of different steps depending upon the structure and purpose of the hydrogel structures. In one example case, the hydrogel structures can be detached from the cells of the spacer substrate and immediately washed with acetone, isopropyl alcohol (IPA), and water to remove unreacted monomers, crosslinkers, and photoinitiators, and suppress photopolymerization and crosslinking reactions. Additionally, to achieve target 3D shapes at an equilibrium swelled state, the hydrogel structures can be immersed in water at 4° C. for 72 hours, or another suitable temperature and duration of time.

At step 110, the process includes shape-morphing the hydrogel structures between different shapes. In general, shape-morphing can be achieved by heating and/or cooling the hydrogel structures. For example, to induce the target 3D shapes at the equilibrium shrunk state, the temperature of the water can be slowly increased to 35° C. Food color dyes can be introduced into the hydrogel structures for imaging, as the hydrogel structures are transparent at equilibrium states without dyes.

In other embodiments, the process in FIG. 10 can be relied upon, at least in part, to prepare air-stable solid structures. As described below, the process can also include the steps of increasing the temperature of the water at step 108, to increase the repulsion of water and transition the hydrogel structures to polymer structures. In some cases, step 108 can also include exchanging the water with an ionic solution, removing the polymer structure from the ionic solution, drying the structure in an oven, and ion deswelling. Additionally, in certain cases, the shape-morphing at step 110 can be omitted entirely.

The use of DL4P for making 3D structures in both swelled and shrunk states is described above. While 3D shape forming and morphing can be conducted in water based on the temperature of the water, the 3D structures can be free (or nearly free) from water at the shrunk (high temperature) state. Thus, in other aspects of the embodiments, a simple approach to remove the 3D structures from the water and into the ambient environment, while preserving the accuracy of the shapes of the structures, is also described below. Further, by incorporating an additional material (e.g. silica, gold, ceramic, etc.) in the form of powder to the precursor, it is possible to achieve hydrogel composites in an aqueous solution and solid polymer matrix composites with desired 3D shapes in the ambient environment.

For the composite structures, the materials can include N-isopropylacrylamide (NIPAm) (97%), N,N'-methylene bisacrylamide (BIS) (99%), poly(ethylene glycol) diacrylate (PEGDA) with the molecular weight of 700 g/mol. Diphenyl (2,4,6-trimethylbenzoyl)phosphine oxide with a wide absorption rage can be used as the photoinitiator. AEROSIL® OX 50 Fumed Silica can be used as the main filler.

The cell can be composed of a PDMS substrate and a cover glass (~150 μm) separated by a 400±0.5 μm PDMS spacer. Precursor solutions can be prepared by dissolving NIPAm (0.4 g), BIS (2.72 mg), and/or PEGDA (3.1 mg) along with diphenyl(2,4,6-trimethylbenzoyl)phosphine oxide (1.8 mg) as photoinitiator in 250 μl of water and 750 μl of acetone. For example, the precursor solutions for composite structures can be prepared by adding an appropriate amount of AEROSIL® OX 50 Fumed Silica at 5, 10, and 20 wt %.

To avoid oxygen interference during polymerization, the precursors can be purged with nitrogen for 1 minute before introducing to the cells. Hydrogel structures can be formed by dynamic light projection grayscale lithography. After exposure, the hydrogel structures can be detached from the cell and immediately washed with IPA and water (0° C.)3 times to suppress further reaction. To remove any unreacted monomer, the structures can be stored in water at low temperature (4° C.) (at the swelled state) for three days while the water being changed every 12 hours.

Figure 11A:
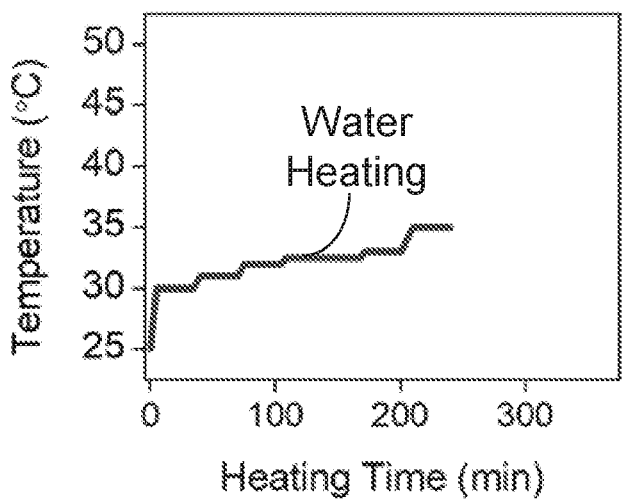
FIGS. 11A-11C illustrate heating hydrogel structures over time to form air-stable polymer structures according to various embodiments described herein.

In one example, after being fully swelled at 4° C. for three days, the hydrogel structures were slowly heated over the lower critical solution temperature (LCST) (~33° C.) as shown in FIG. 11A and kept for 12 hours to ensure most of the water was excluded due to the LCST transition. At temperatures over the LCST, the hydrogel structures can start to loose water and the programmed formation leads to desired 3D shape. Using liquid desiccants like high MW PEG can help avoiding the skin effect during the phase separation transition.

Figure 11B:
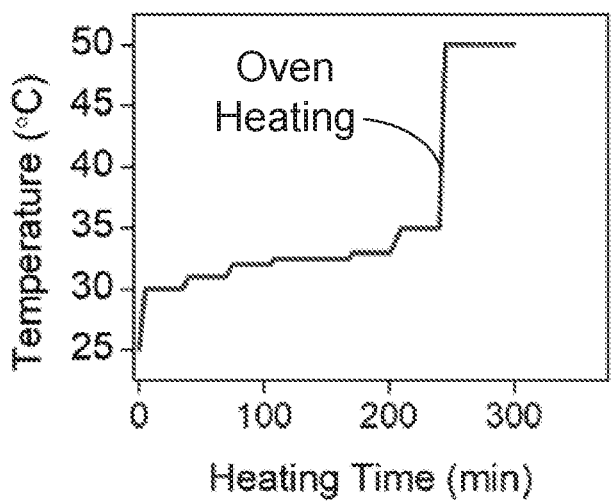

Although the hydrogel structures are at the shrunk state at temperatures higher than LCST, they can still contain a small amount of water which may deform the hydrogel structures when they are transferred from water to the ambient environment. Thus, to further exclude water, the temperature of the water can be further increased. The water temperature can be increased to 50° C. or higher as shown in FIG. 11B.

However, even if the water is completely excluded from the hydrogel structures, the water on the surface still can deform the hydrogel structures if it remains on the surface and cools down to a temperature lower than LCST. One can solve this problem by further increasing the temperature so that the surface temp maintains higher than LCST before being blotted. However, this would be hard to achieve for big samples of hydrogel structures or hydrogel structures with complex geometries that may hold the water on the surface.

Figure 11C:
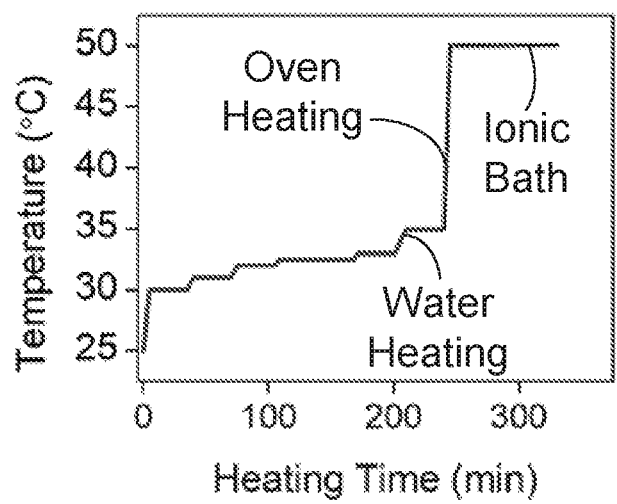

Thus, in another example, to avoid water on the surfaces of the hydrogel structures in ambient air, the hydrogel structures can be introduced to a near saturated ionic aqueous solution before exposing them to ambient air. The concentrated ionic environment can help maintain the samples at the shrunk state even at ambient temperatures. Thus, after soaking the structures in water for one hour at 50° C., the water medium can be changed to a near saturated sodium salt solution at 50° ° C. as shown in FIG. 11C. The hydrogel structures can then be removed from the solution to ambient air after 30 min of soaking in the ionic environment. The hydrogel structures can then be placed on an absorbent tissue in ambient air to remove as much water as possible. The unique chemistry of the process enables a 3D structure to maintain its structure outside the water environment.

Figure 12:
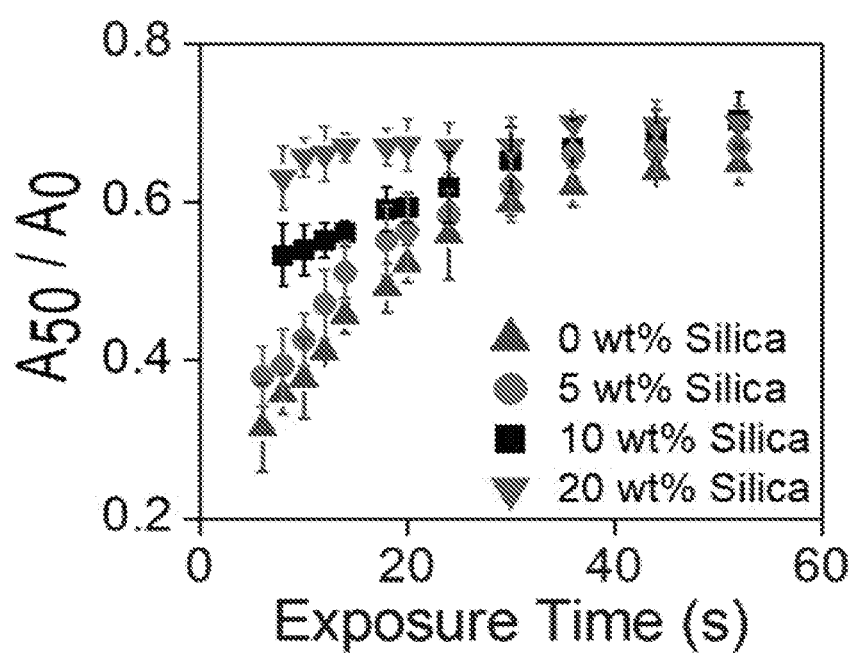
FIG. 12 illustrates calibration curves for precursor solutions including different amounts of solid material (silica) to form polymer composite structures according to various embodiments described herein.

To prepare the solid composite structures, the calibration curves for different amounts of solid material can be used. FIG. 12 shows the calibration curves to form hydrogel composite structures and air-stable polymer composite structures from the precursor solutions containing different amounts of silica powders at the shrunk state.

Although embodiments have been described herein in detail, the descriptions are by way of example. The features of the embodiments described herein are representative and, in alternative embodiments, certain features and elements may be added or omitted. Additionally, modifications to aspects of the embodiments described herein may be made by those skilled in the art without departing from the spirit and scope of the present invention defined in the following claims, the scope of which are to be accorded the broadest interpretation so as to encompass modifications and equivalent structures.

At least the following is claimed:

1. A method of forming hydrogel structures with programmed 3D shapes, comprising:
    preparing a precursor solution;
    introducing the precursor solution into a cell;
    exposing the precursor solution in the cell with light;
    spatially and temporally controlling the exposure of the precursor solution using dynamic light projection grayscale lithography and a growth function or a growth pattern that can induce a target 3D structure and motion to form a hydrogel structure from the precursor solution that comprises continuously varying, spatially controlled compositions and material properties; and
    shape-morphing the hydrogel structure to form a prescribed shape by heating or cooling the hydrogel structure.

2. The method of claim 1, wherein the precursor solution comprises a solution comprising monomers, two or more cross linkers with different chain lengths, at least one photoinitiator, and at least one solvent.

3. The method of claim 1, wherein the precursor solution comprises a solution of N-isopropylacrylamide (NIPAm), N,N'-methylene bisacrylamide (BIS), poly(ethylene glycol) diacrylate (PEGDA), diphenyl(2,4,6-trimethylbenzoyl) phosphine oxide, water, and acetone.

4. The method of claim 1, wherein spatially and temporally controlling exposure of the precursor solution using the dynamic light projection grayscale lithography forms the hydrogel structure with spatially controlled material properties, including degrees and rates of swelling and shrinking, described by a growth function or a growth pattern.

5. The method of claim 1, wherein:
    the precursor solution comprises a solution of N-isopropylacrylamide (NIPAm), N,N'-methylene bisacrylamide (BIS), and poly(ethylene glycol) diacrylate (PEGDA); and
    spatially and temporally controlling exposure of the precursor solution using the dynamic light projection grayscale lithography forms a hydrogel structure with continuously varying, spatially controlled compositions and material properties, including degrees and rates of swelling and shrinking, using a growth function or a growth pattern.

6. The method of claim 1, further comprising generating calibration curves of areal swelling and shrinking ratios versus light exposure time to convert a growth function or a growth pattern into a spatially controlled light exposure time.

7. The method of claim 1, wherein the cell comprises a substrate with a spacer formed of polydimethylsiloxane (PDMS).

8. The method of claim 1, further comprising, before introducing the precursor solution into the cell, purging the solution with nitrogen to reduce the effect of oxygen on photopolymerization of the precursor solution.

9. A method of forming hydrogel structures with programmed 3D shapes, comprising:
    generating calibration curves of areal swelling and shrinking ratios versus light exposure time to convert a growth function or a growth pattern into a spatially controlled light exposure time;
    preparing a precursor solution;
    introducing the precursor solution into a cell;
    exposing the precursor solution in the cell with light;
    spatially and temporally controlling the exposure of the precursor solution using the generated calibration curves to form a hydrogel structure from the precursor solution that comprises continuously varying, spatially controlled compositions and material properties; and
    shape-morphing the hydrogel structure to form a prescribed shape by heating or cooling the hydrogel structure.

10. A method of forming hydrogel structures with programmed 3D shapes, comprising:
    preparing a precursor solution;
    introducing the precursor solution into a cell;
    exposing the precursor solution in the cell with light; and
    spatially and temporally controlling the exposure of the precursor solution using dynamic light projection grayscale lithography and a growth function or a growth pattern that can induce a target 3D structure to form a hydrogel structure from the precursor solution that comprises continuously varying, spatially controlled compositions and material properties.

11. The method of claim 10, wherein the growth function or growth pattern can further induce a target motion.

12. The method of claim 11, wherein the hydrogel structure can morph to form prescribed shapes when heated or cooled.

13. The method of claim 10, wherein the precursor solution comprises a solution comprising monomers, two or more cross linkers with different chain lengths, at least one photoinitiator, and at least one solvent.

14. The method of claim 10, wherein the precursor solution comprises a solution of N-isopropylacrylamide (NIPAm), N,N'-methylene bisacrylamide (BIS), and poly(ethylene glycol) diacrylate (PEGDA).

15. The method of claim 10, wherein spatially and temporally controlling exposure of the precursor solution provides the hydrogel structure with spatially controlled degrees and rates of swelling and shrinking, described by the growth function or growth pattern.

\* \* \* \* \*